(12) United States Patent
Fehr et al.

(10) Patent No.: US 7,196,050 B2
(45) Date of Patent: Mar. 27, 2007

(54) UNSATURATED ESTER AS PERFUMING INGREDIENT

(75) Inventors: Charles Fehr, Versoix (CH); Pierre-Alain Blanc, Crassier (CH)

(73) Assignee: Firmenich SA, Geneva (CH)

( * ) Notice: Subject to any disclaimer, the term of this patent is extended or adjusted under 35 U.S.C. 154(b) by 464 days.

(21) Appl. No.: 10/285,418

(22) Filed: Nov. 1, 2002

(65) Prior Publication Data

US 2003/0119712 A1 Jun. 26, 2003

(30) Foreign Application Priority Data

Dec. 5, 2001 (WO) .................. PCT/IB01/02394

(51) Int. Cl.
*A61K 8/18* (2006.01)
(52) U.S. Cl. .............. 512/25; 512/8; 512/26
(58) Field of Classification Search ......... 512/25, 512/26, 8
See application file for complete search history.

(56) References Cited

U.S. PATENT DOCUMENTS

| | | | | |
|---|---|---|---|---|
| 3,887,625 A | | 6/1975 | Schulte-Elte | ............... 260/617 |
| 4,113,663 A | * | 9/1978 | Schenk | ...................... 512/24 |
| 4,411,829 A | * | 10/1983 | Schulte-Elte et al. | ........ 512/24 |
| 4,460,792 A | | 7/1984 | Schulte-Elte et al. | ....... 568/341 |
| 4,900,870 A | | 2/1990 | Fehr et al. | ................. 568/354 |
| 5,015,625 A | * | 5/1991 | Fehr et al. | ..................... 512/24 |
| 5,288,702 A | * | 2/1994 | Ogura et al. | ................. 512/24 |
| 5,614,486 A | * | 3/1997 | Giersch et al. | .............. 512/21 |
| 6,589,921 B2 | * | 7/2003 | Herrmann et al. | ......... 510/102 |

FOREIGN PATENT DOCUMENTS

| | | |
|---|---|---|
| DE | 2 305 140 | 8/1973 |
| DE | 32 33 175 A1 | 3/1983 |
| EP | 0 056 109 B1 | 1/1986 |

* cited by examiner

*Primary Examiner*—Monique T. Cole
(74) *Attorney, Agent, or Firm*—Winston & Strawn LLP

(57) ABSTRACT

The present invention relates to a compound of formula

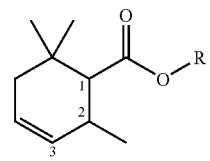

(I)

wherein R represents a methyl or an ethyl group, in the form of any one of its isomers or of a mixture thereof. The invention relates also to the use of such a compound as a perfuming ingredient capable of imparting a odorant note of the rose type. Moreover, the invention concern also the perfumed article or perfuming composition containing a compound according to the invention.

5 Claims, No Drawings

UNSATURATED ESTER AS PERFUMING INGREDIENT

BRIEF SUMMARY OF THE INVENTION

The present invention relates to the perfume industry. It concerns more particularly a compound of formula

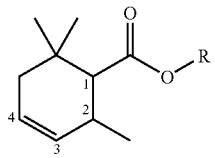
(I)

wherein R represents a methyl or an ethyl group, in the form of any one of its isomers or of a mixture thereof. The invention also relates to the use of such a compound as a perfuming ingredient and to the perfumed article or perfuming composition containing a compound according to the invention.

PRIOR ART

Although several similar structures are known in the literature, to the best of our knowledge, the compounds of the present invention have novel chemical structures.

A 1/1 mixture of ethyl esters of formula (I) having the carbon-carbon double bond in position 3 or 4 of the ring is described in U.S. Pat. No. 3,887,625. However in said document there are no useful indications that could allow a person skilled in the art to obtain an ester according to the invention (e.g. having the carbon-carbon double bond only in position 3). Furthermore, in the prior art there is no mention or suggestion of any organoleptic properties of the compounds of formula (I), or of any potential use of said compounds as perfuming ingredients.

DETAILED DESCRIPTION OF THE PREFERRED EMBODIMENTS OF THE INVENTION

Surprisingly, we have now established that the compounds of formula

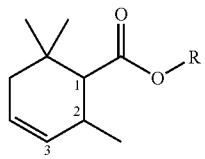
(I)

wherein R represents a methyl or an ethyl group, in the form of any one of its isomers, namely the (1R,2R), (1R,2S), (1S,2R) or the (1S,2S) isomers, or of a mixture thereof, possess a surprising and very useful damascone-like fragrance, which render them very convenient for the preparation of perfumes, perfuming compositions and perfumed products.

Amongst the compounds of formula (I), the methyl trans-2,6,6-trimethyl-3-cyclohexene-1-carboxylate is much appreciated for its odor which presents a remarkable damascone, rosy note associated with citronellol like and slightly saffrony notes. The damascone note is particularly nice and has a very natural, very rosy, more precisely red rose odor. Moreover, said odor is devoid of the fermented-apple aspect present for example in the alpha damascone fragrance. From an olfactory point of view, the odor character of methyl trans-2,6,6-trimethyl-3-cyclohexene-1-carboxylate is intermediate between that of delta and alpha damascone. Nevertheless, and despite this odor similarity, the use of the invention compounds has been proved to be more versatile than that of the damascones.

Furthermore, perfumers have also noticed some differences between the two enantiomers of the trans methyl ester, namely the (1R,2S) and the (1S,2R) methyl 2,6,6-trimethyl-3-cyclohexene-1-carboxylate. Indeed, although the odor of both enantiomers is clearly damascone-like and in the same trend described hereinabove, the fragrance of the (1R,2S) enantiomer is stronger that the one of the (1 S,2R) enantiomer which, in the other hand, is more aromatic.

In addition to the typical rose, damascone-like note of the compounds of formula (I), the methyl cis-2,6,6-trimethyl-3-cyclohexene-1-carboxylate possesses also terpenic and carrot tops notes.

The ethyl trans-2,6,6-trimethyl-3-cyclohexene-1-carboxylate develops a damascone-like odor similar to that of the corresponding trans methyl ester. The similarity of the odor of the ethyl and methyl ester is quite surprising in view of the prior art, wherein the methyl and ethyl esters of known analogues have in general significantly different odor properties.

The preferred compounds of the invention are the methyl trans-2,6,6-trimethyl-3-cyclohexene-1-carboxylate and the (1R,2S) methyl 2,6,6-trimethyl-3-cyclohexene-1-carboxylate.

The character and the quality of the odor properties of the invention compounds are all the more surprising and unexpected in view of the odor of their prior art analogues.

Indeed, the trans methyl ester of formula (I) possesses an odor closer to that of damascones than its gamma or alpha isomers, namely methyl 2,2-dimethyl-6-methylene-1-cyclohexanecarboxylate (described in U.S. Pat. No. 5,015,625, to Firmenich SA) and methyl 2,6,6-trimethyl-2-cyclohexene-1-carboxylate (described in EP 56109) respectively. This effect is mainly due to the fact that, when compared with the mentioned isomers, the trans methyl ester presents a more pure damascone-rosy connotation, which is almost devoid of the typical herbaceous-thujonic and red-fruity, green apple notes of said gamma and alpha isomer.

Similarly, when the trans ethyl ester of formula (I) is compared with the ethyl gamma isomer, also described in U.S. Pat. No. 5,015,625, then the invention compound distinguishes itself from the prior known compound in that it presents a rosy odor devoid of the metallic, herbaceous-thujonic notes characteristic of the prior art analogue.

The compounds of the invention are suitable for use in fine perfumery, in perfumes, colognes or after-shave lotions, as well as in other current uses in perfumery such as to perfume soaps, preparations for the shower or the bath, such as bath salts, mousses, oils, gels or other preparations, products such as body oils, body-care products, body deodorants and antiperspirants, hair care products such as shampoos, ambient air deodorants, or cosmetic preparations.

The compounds of formula (I) can also be used in applications such as liquid or solid detergents for textile treatment, fabric softeners, or also in detergent compositions or cleaning products for cleaning dishes or varied surfaces, for industrial or household use.

In these applications, the compounds according to the invention can be used alone, as well as mixed with other perfuming ingredients, solvents, adjuvants or additives commonly used in perfumery. The nature and variety of these co-ingredients do not require a more detailed description here, which would not be exhaustive anyway. In fact, a person skilled in the art, having a general knowledge, is able to choose them according to the nature of the product that has to be perfumed and the olfactory effect sought. These perfuming co-ingredients belong to varied chemical groups such as alcohols, aldehydes, ketones, esters, ethers, acetates, nitrites, terpenic hydrocarbons, heterocyclic nitrogen- or sulfur-containing compounds, as well as natural or synthetic essential oils. Many of these ingredients are listed in reference texts such as S. Arctander, Perfume and Flavor Chemicals, 1969, Montclair, N.J., USA, or more recent versions thereof, or in other similar books, or yet in the specialized patent literature commonly available in the art.

The proportions in which the compounds according to the invention can be incorporated in the different products mentioned above vary in a broad range of values. Indeed, we have found that the compounds of the invention are environmentally friendly and not sensitizing, and this even at relatively high concentrations. The range of concentrations depends on the nature of the product to be perfumed and on the olfactory effect sought, as well as on the nature of the co-ingredients in a given composition when the compounds of the invention are used in admixture with perfuming co-ingredients, solvents or additives commonly used in the art.

For instance, concentrations from 0.1% to 1.5%, and preferably from 0.3% to 0.8%, by weight of these compounds, with respect to the perfuming composition in which they are incorporated, can be typically used. Lower concentrations than these can be used when these compounds are directly applied for perfuming some of the consumer products mentioned above.

The synthesis of the compounds of formula (I), which is another object of the present invention, is characterized by a rearrangement reaction which provides directly a final product having a carbon-carbon double bond selectively in the position 3. Said rearrangement reaction is characterized by the reaction of a α-β unsaturated tosyl hydrazone of formula

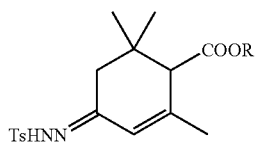

(II)

wherein R represents a methyl or ethyl group, in the presence of a borane derivative, such as $NaBH_4$ or catechol borane $((C_6H_4O_2)BH)$, and a carboxylate derivative selected in the group consisting of the $C_1$–$C_8$ carboxylic acids and their alkaline salts. Preferably the borane derivative is catechol borane and the carboxylate derivative is a sodium or potassium salt of a $C_2$–$C_4$ carboxylic acid.

This synthesis provides the compounds of formula (I) as a mixture of four possible isomers. The two diastereomers, namely the trans and cis isomers, may be subsequently separated by using conventional methods, such as recrystallization or chromatography. Finally, the enantiomers of each diastereomer may be separated by recrystallisazion of the ephedrate salt of the free acid derivative, as will be described in the examples.

The invention will now be described in further detail by way of the following examples, wherein the temperatures are indicated in degrees centigrade (°C.); the NMR spectral data were recorded with a 360 MHz machine in $CDCl_3$; the chemical displacement δ are indicated in ppm with respect to the TMS as standard and all the abbreviations have the usual meaning in the art.

DESCRIPTION OF THE INVENTION

EXAMPLE 1

Synthesis of methyl (Trans/Cis) 2,6,6-trimethyl-3-cyclohexene-1-carboxylate a) Methyl 2,2,6-trimethyl-4-[(4-methylphenylsulfonyl)hydrazono]-2-cyclohexene-1-carboxylate A suspension of p-toluenesulfonylhydrazide (96.80 g, 0.520 mol) in a solution of methyl 2,2,6-trimethyl-4-oxo-2-cyclohexene-1-carboxylate (92.71 g, 0.473 mol) and AcOH (0.463 g, 4.7 mmol) in MeOH (500 ml) was heated at reflux in a 1.5 l three necked flask, fitted with a mechanical stirrer.

Upon heating the reaction mixture became clear and, once at reflux temperature, the formed hydrazone gradually precipitated. Heating was prolonged for 6 h, then the reaction mixture was cooled at 0° and the precipitated solid was collected by filtration affording 153.80 g of pure hydrazone. Crystallization of the mother liquors from MeOH (55 ml) gave a second portion of pure hydrazone (2.90 g) (yield=91%).

$^1$H-NMR: 0.92(s, 3H); 1.02(s, 3H); 1.80(s, 3H); 2.13(d, J=16.0, 1H); 2.39(d, J=16.0, 1H); 2.77(s, 3H); 3.66(s, 3H); 6.08(s, 1H); 7.29(d, J=8.0 Hz, 2H); 7.84(d, J=8.0, 2H).

$^{13}$C-NMR: 172.3(s); 154.1(s); 144.0(s); 140.3(s); 135.4(s); 129.6(d); 128.0(d); 124.5(d); 57.5(d); 51.92(q); 33.7(t); 33.4(s); 28.4(q); 27.3(q); 23.1(q); 21.6(q).

b) Methyl 2,6,6-trimethyl-3-cyclohexene-1-carboxylate and separation of trans and cis Diastereomers In a three necked 2 l flask fitted with a mechanical stirrer, catechol borane (15.25 g, 0.126 mol) was added in 15 minutes, at 0° C., to a suspension of the hydrazone obtained in a) (38.45 g, 0.105 mol) in $CHCl_3$ (500 ml). After 2 hours, to the yellow reaction mixture, still at 0° C., $AcONa.3H_2O$ (28.7 g, 0.211 mol) was added at once. After 30 minutes, the reaction mixture was heated at reflux for 1 hour, then cooled at 25° and the white solid filtered off on Celite. The cake was washed with three portions of $CHCl_3$, and the combined filtrates were evaporated under reduced pressure. The crude material was dissolved in pentane, the organic layer washed (5% aqueous NaOH, $H_2O$ and brine), dried ($Na_2SO_4$), filtered and concentrated. Bulb-to-bulb distillation (75–120°/3 mbar) of the crude product afforded 8.55 g of methyl 2,6,6-trimethyl-3-cyclohexene-1-carboxylate as a trans/cis=86:14 mixture (yield=43%).

Crystallization of the thus obtained product, at −78° from pentane (9.5 ml), afforded 6.39 g of methyl trans-2,6,6-trimethyl-3-cyclohexene-1-carboxylate (trans/cis=96:4), and concentration of the crystallization mother liquors gave 2.13 g of methyl 2,6,6-trimethyl-3-cyclohexene-1-carboxylate in the form of a trans/cis=54:46 mixture.

Two flash chromatograph separations (SiO$_2$, cyclohexane/AcOEt=97:3) of the compounds issued from the mother liquors gave 0.9 g of the cis diastereomer as a trans/cis=10:90 mixture.

Methyl trans-2,6,6-trimethyl-3-cyclohexene-1-carboxylate
$^1$H-NMR: 0.93(d, J=6.5, 3H); 0.95(s, 3H); 0.99(s, 3H); 1.74(d, J=18.0, 1H); 1.95(d, J=18.0, 1H); 2.04(d, J=11.5, 1H); 2.52(m, 1H); 3.69(s, 3H); 5.47(d, J=10.0, 1H); 5.52–5.59(m, 1H).
$^{13}$C-NMR: 175.3(s); 131.1(d); 124.4(d); 57.6(d); 51.0(q); 41.1(t); 32.3(s); 31.6(d); 29.6(q); 20.9(q); 20.0(q).
MS: 182(M$^+$, 20); 151(10); 127(14); 126(16); 125(41); 123(66); 122(93); 114(13); 111(23); 108(17); 107(100); 96(13); 95(23); 93(22); 91(37); 83(19); 82(30); 81(43); 79(28); 77(27); 69(21); 68(28); 67(43); 65(16) 59(16); 55(21); 53(24); 51(10); 43(16); 39(41); 29(21); 27(22);

Methyl cis-2,6,6-trimethyl-3-cyclohexene-1-carboxylate
$^1$H-NMR: 0.95(s, 3H); 0.97(s, 3H); 0.98(d, J=7.5, 3H); 1.66(d, J=18.0, 1H); 2.28(d, J=18.0, 1H); 2.37(d, J=6.0, 1H); 2.52(m, 1H); 3.61(s, 3H); 5.40(d, J=10.0, 1H); 5.65–5.73(m, 1H).
$^{13}$C-NMR: 173.9(s); 128.2(d); 125.8(d); 54.6(d); 50.6(q); 35.6(t); 31.3(s); 29.6(d); 29.5(q); 29.0(q); 17.7(q).
MS: 182(M$^+$, 24); 167(10); 151(13); 127(16); 126(19); 125(43); 122(100); 114(14); 111(20); 108(15); 107(89); 95(18); 93(16); 91(25); 83(15); 82(28); 81(32); 79(16); 77(15); 69(18); 68(24); 67(30); 55(11); 53(11); 41(19); 39(11).

EXAMPLE 2

Synthesis of the enantiomers of the methyl trans 2,6,6-trimethyl-3-cyclohexene-1-carboxylate a) (±)-trans-2,6,6-trimethyl-3-cyclohexene-1-carboxylic acid
A suspension of KOH (4.34 g, 77.5 mmol) in a solution of methyl trans 2,6,6-trimethyl-3-cyclohexene-1-carboxylate (13.48 g, 74.1 mmol) and thiophenol (8.51 g, 77.5 mmol) in DMF (60 ml) was heated at 100° in a three necked 250 ml flask fitted with a stirrer. After 16 hours, the cooled mixture was poured onto cold aqueous HCl (0.5 M, 200 ml) and extracted with Et$_2$O. The crude compound was pre-purified by standard acid-base extraction. The organic phase was dried (Na$_2$SO$_4$), filtered, concentrated, and then heated for 4 h at 100°/4 mbar to remove the excess of thiophenol. Bulb-to-bulb distillation (100–130°/0.1 mbar) afforded 10.57 g of the racemic acid as a trans/cis=96:4 mixture (yield=85%).
$^1$H-NMR: 1.02(s, 3H); 1.03(d, J=7.6 Hz, 3H); 1.05(s, 3H); 1.77(d, J=18.0, 1H); 1.97(d, J=18.0, 1H); 2.04(d, J=10.0, 1s); 2.50(m, 1s); 5.47(d, J=10.0, 1H); 5.53–5.60(m, 1H); 11.35–11.85(s, 1H).
$^{13}$C-NMR: 181.4(s); 130.9(d); 124.4(d); 57.6(d); 41.1(t); 32.2(s); 31.1(d); 29.5(q); 20.9(q); 20.0(q).
MS: 168(M$^+$, 91); 153(33); 125(34); 124(58); 113(58); 112(46); 111(100); 109(36); 108(20); 107(83); 101(13); 100(27); 97(26); 95(25); 91(36); 83(13); 82(65); 81(44); 79(24); 77(24); 69(58); 68(52); 67(60); 65(13); 56(18); 55(15); 53(13); 43(13); 41(24); 39(16).

b) (−)-trans-2,6,6-trimethyl-3-cyclohexene-1-carboxylic acid
In a 100 ml flask equipped with a mechanical stirrer, a solution of (−)-ephedrine (Fluka, 5.64 g, 34.2 mmol) in an hexane-acetone mixture (75:25, 27 ml) was added in 5 minutes to a solution of (±)-trans-2,6,6-trimethyl-3-cyclohexene-1-carboxylic acid (7.65 g, 45.5 mmol) in hexane (20 ml). After stirring for 45 minutes, the suspension vas cooled at 0° and filtered to afford 5.61 g of ephedrate salt (65% ee) and a mother liquor. Two crystallizations of the ephedrate salt from a toluene-hexane mixture (60:40) afforded 4.08 g of pure ephedrate salt and the corresponding mother liquors. The pure ephedrate salt thus obtained was dissolved in methanol (45 ml) and treated at 25° with 5% aqueous HCl (10.5 ml). After half an hour, the reaction mixture was concentrated and the residue dissolved in AcOEt (100 ml). The organic phase was washed (H$_2$O and brine), dried (Na$_2$SO$_4$), filtered and concentrated. A bulb-to-bulb distillation (100–130°/0.1 mbar) afforded 2.01 g of pure (−)-trans-2,6,6-trimethyl-3-cyclohexene-1-carboxylic acid (98% ee determined by chiral GC on CP-Chirasil-DEX CB).
$[\alpha]_D^{20}$ (CHCl$_3$, c=14 g/l)=−97.3
NMR: as previously described for the racemic compound.

c) (+)-trans-2,6,6-trimethyl-3-cyclohexene-1-carboxylic acid
The combined mother liquors obtained in b) (9.14 g of salt) were regenerated using the same procedure as described in b) to provide the free acid. A bulb-to-bulb distillation (100–130° C./0.1 mbar) afforded 5.20 g of (+)-trans-2,6,6-trimethyl-3-cyclohexene-1-carboxylic acid (ee=41%). The free acid was thus treated with (+)-ephedrine hemihydrate (Sigma, 5.39 g, 31.0 mmol) as described herein above for the other enantiomer to obtain 8.91 g of ephedrate salt (49% ee). Two crystallizations, as descibed in b), of the salt afforded 5.55 g of pure salt (97% ee). The pure ephedrate salt thus obtained was dissolved in methanol (58 ml) and trated with 5% aqueous HCl (14.5 ml). After half an hour, the reaction mixture was concentrated and the residue dissolved in AcOEt (100 ml). The organic phase was washed (H$_2$O and brine), dried (Na$_2$SO$_4$), filtered and concentrated. A bulb-to-bulb distillation (100–130°/0.1 mbar) afforded 2.01 g of pure (+)-trans-2,6,6-trimethyl-3-cyclohexene-1-carboxylic acid (98% ee determined by chiral GC on CP-Chirasil-DEX CB).
$[\alpha]_D^{20}$ (CHCl$_3$, c=12 g/l)=+100.9
NMR: as previously described for the racemic compound.

d) (+) or (−)-methyl trans-2,6,6-trimethyl-3-cyclohexene-1-carboxylate
In a three necked 100 ml flask, a solution of the desired enantiomer of free acid obtained in b) or c) (1.85 g, 1.0 mmol), methyliodide (1.87 g, 15.8 mmol), and K$_2$CO$_3$ (1.82 g, 15.8 mmol) in DMF (40 ml) was stirred at 40° C. for 2 hours. The cooled reaction mixture was poured onto cold 5% aqueous HCl and extracted twice with pentane. The organic phases were washed (three times with H$_2$O and brine), dried (Na$_2$SO$_4$), filtered and concentrated. A bulb-to-bulb distillation (100°/4 mbar) afforded 1.8 g of desired methyl ester (yield=90%).
(−)-Methyl (1S,2R)-2,6,6-trimethyl-3-cyclohexene-1-carboxylate
$[\alpha]_D^{20}$ (CHCl$_3$, c=28 g/l)=−83.3
NMR: as previously described for the racemic compound.
(+)-Methyl (1R,2S)-2,6,6-trimethyl-3-cyclohexene-1-carboxylate
$[\alpha]_D^{20}$ (CHCl$_3$, c=29 g/l)=−83.1
NMR: as previously described for the racemic compound.

EXAMPLE 3

Synthesis of ethyl trans 2,6,6-trimethyl-3-cyclohexene-1-carboxylate
In a three necked 100 ml flask a suspension of trans-2,6,6-trimethyl-3-cyclohexene-1-carboxylic acid obtained in example 2 a) (0.800 g, 4.8 mmol), ethylbromide (0.616 g, 5.7 mmol) and K$_2$CO$_3$ (0.787 g, 5.7 mmol) in DMF (20 ml) was stirred at 40° C. for 2 h. The cooled reaction mixture was next poured onto cold 5% aqueous HCl and extracted twice with pentane. The organic phases were washed (three times with H$_2$O and brine), dried (Na$_2$SO$_4$), filtered and concentrated. A bulb-to-bulb distillation (100°/4 mbar) afforded 0.870 g of ethyl trans 2,6,6-trimethyl-3-cyclohexene-1-carboxylate in the form of a trans/cis=96:4 mixture (yield=84%).

$^1$H-NMR: 0.94(d, J=6.5, 3H); 0.96(s, 3H); 0.99(s, 3H); 1.28(t, J=7.6, 3H); 1.73(d, J=18.0, 1H); 1.96(d, J=18.0, 1H); 2.02(d, J=10.4, 1H); 2.52(m, 1H); 4.16(q, J=7.6, 2H); 5.46 (d, J=10.0, 1H); 5.52–5.59(m, 1H).

$^{13}$C-NMR: 174.7(s); 131.2(d); 124.3(d); 59.8(t); 57.7(d); 41.2(t); 32.3(s); 31.3(d); 29.4(t); 20.9(q); 19.9(q); 14.4(q).

MS: 196(23); 151(17); 139(18); 123(84); 122(100); 121 (21); 112(25); 111(15); 108(14); 107(86); 95(15); 93(22); 91(30); 83(10); 82(22); 81(45); 79(23); 77(22); 69(15); 68(18); 67(32); 65(13); 55(18); 53(17); 42(18); 41(38); 39(26); 29(38); 27(24).

EXAMPLE 4

Preparation of a Perfuming Composition

A "fruity" type base composition was prepared by admixing the following ingredients:

| Ingredient | Parts by weight |
| --- | --- |
| 10%* Amyl acetate | 10 |
| 10%* 3-Methyl-2-butenyl acetate | 30 |
| 10%* Aldehyde C6 | 30 |
| Hexylcinnamic aldehyde | 100 |
| Ethyl anthranilate | 5 |
| 2-Methyl-4-phenyl-2-butanol | 30 |
| Methyl cinnamate | 10 |
| 10%* Cis-3-hexenol | 30 |
| Dihydro Eugenol | 5 |
| 10%* β-Dorinone® [1] | 20 |
| Diethyl 1,4-cyclohexanedicarboxylate [2] | 60 |
| Habanolide® [3] | 60 |
| Hedione® [4] | 120 |
| Alpha ionone | 50 |
| 10%* Cis-3-hexenol isobutyrate | 20 |
| Phenylethyl isobutyrate | 30 |
| 10%* Cognac oil | 20 |
| Methyl isoeugenol | 20 |
| Muscenone Delta [5] | 10 |
| Florol® [6] | 50 |
| Phenethylol | 150 |
| Cis-3-hexenol salicylate | 10 |
| 10%* Vanilline | 25 |
| Bergamot essential oil | 40 |
| Parmantheme [7] | 5 |
|  | 940 |

*in dipropyleneglycol
[1] 1-(2,6,6-trimethyl-1-cyclohexen-1-yl)-2-buten-1-one; origin: Firmenich SA, Geneva, Switzerland
[2] origin: Firmenich SA, Geneva, Switzerland
[3] pentadecenolide; origin: Firmenich SA, Geneva, Switzerland
[4] methyl dihydrojasmonate; origin: Firmenich SA, Geneva, Switzerland
[5] 3-methyl-(4 and 5)-cyclopentadecen-1-one; origin: Firmenich SA, Geneva, Switzerland
[6] tetrahydro-2-isobutyl-4-methyl-4(2H)-pyranol; origin: Firmenich SA, Geneva, Switzerland
[7] perfumery base; origin: Firmenich SA, Geneva, Switzerland The addition of 100 parts by weight of methyl trans-2,6,6-trimethyl-3-cyclohexene-1-carboxylate to the above-described composition imparted to the latter a pronounced rose connotation. The olfactory effect provided by the addition of the invention compound is similar to that provided by 6-damascone. Moreover, this olfactory effect was less fruity-blackberry-blueberry than the one obtained by adding the same amount of the prior known gamma isomer (methyl 2,2-dimethyl-6-methylene-1-cyclohexanecarboxylate), and was also more elegant and more damascone-like than the effect that can be obtained with the other known structural analogues, e.g. the alpha isomer of the invention compound.

EXAMPLE 5

Preparation of a Perfuming Composition

An "aromatic" type composition was prepared by admixing the following ingredients:

| Ingredient | Parts by weight |
| --- | --- |
| Allyl amyl glycolate | 30 |
| Bergamot essential oil | 100 |
| Cetalox® [1] | 10 |
| Coumarine | 10 |
| Dihydromyrcenol | 300 |
| Estragol | 10 |
| Exaltenone [2] | 30 |
| 10%* Galbanum essential oil | 10 |
| Hedione® HC [3] | 70 |
| Habanolide® [4] | 80 |
| 10%* Isobutylquinoleine | 40 |
| Lavandin essential oil | 40 |
| Crystal moss | 40 |
| Polysantol® [5] | 20 |
| Patchouli essential oil | 80 |
| 10%* Triplal [6] | 40 |
| Galbex® [7] 183 | 60 |
|  | 970 |

*in dipropyleneglycol
[1] 8,12-epoxy-13,14,15,16-tetranorlabdane; origin: Firmenich SA, Geneva, Switzerland
[2] (Z)-4-cyclopentadecen-1-one; origin: Firmenich SA, Geneva, Switzerland
[3] methyl dihydrojasmonate; origin: Firmenich SA, Geneva, Switzerland
[4] pentadecenolide; origin: Firmenich SA, Geneva, Switzerland
[5] 3,3-dimethyl-5-(2',2',3'-trimethyl-3'-cyclopenten-1'-yl)-4-penten-2-ol; origin: Firmenich SA, Geneva, Switzerland
[6] origin: IFF, USA
[7] origin: Firmenich SA, Geneva, Switzerland The addition of 300 parts by weight of methyl trans-2,6,6-trimethyl-3-cyclohexene-1-carboxylate to the above-described composition imparted to the latter a fruity, green, damascone-like, rosy odor. This effect was reminiscent of the fragrance generally imparted by delta damascone, but it was at the same time more fruity and less floral.

EXAMPLE 6

Preparation of a Perfuming Composition

A "fruity-citrus" type base composition was prepared by admixing the following ingredients:

| Ingredient | Parts by weight |
| --- | --- |
| Benzyl acetate | 20 |
| Geranyl acetate | 20 |
| Linalyl acetate | 150 |
| 10%* 2-Methyldecanal | 20 |
| Dihydromyrcenol | 140 |
| Habanolide® [1] | 20 |
| Lemongrass | 15 |
| Limette | 20 |
| Liminal® [2] | 5 |
| Linalool | 100 |
| Hedione® [3] | 60 |
| Muscenone 4) | 20 |

-continued

| Ingredient | Parts by weight |
| --- | --- |
| 10%** (Z)-3-Decenal [5] | 30 |
| 10%* Oxane [6] | 10 |
| 10%* Rose oxide | 20 |
| Orange essential oil | 300 |
| | 950 |

*in dipropyleneglycol
**in ethyl citrate
[1] pentadecenolide; origin: Firmenich SA, Geneva, Switzerland
[2] 1-p-menthene-9-carbaldehyde; origin: Firmenich SA, Geneva, Switzerland
[3] methyl dihydrojasmonate; origin: Firmenich SA, Geneva, Switzerland
[4] 3-methyl-(4 and 5)-cyclopentadecen-1-one; origin: Firmenich SA, Geneva, Switzerland
[5] origin: Firmenich SA, Geneva, Switzerland
[6] cis-2-methyl-4-propyl-1,3-oxathiane; origin: Firmenich SA, Geneva, Switzerland The addition of 50 parts by weight of methyl trans-2,6,6-trimethyl-3-cyclohexene-1-carboxylate to the above-described base composition imparted to the latter a rosy and red apple effect. When the gamma or the alpha isomers were used instead of the compound of the invention, the effect was aromatic-rosemary and fruity-blueberry, or more cellar, herbaceous and earthy, respectively.

The invention claimed is:

1. A method to improve, enhance or modify the floral odor of a perfume or a perfuming composition without imparting a fruity note thereto, which method comprises adding to said perfume or composition a fragrant effective amount of a compound of formula

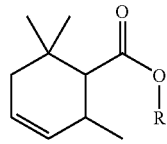

(I)

wherein R represents a methyl or an ethyl group, in the form of any one of its isomers or of a mixture thereof.

2. The method of claim 1, wherein the compound provides the floral odor to a perfuming composition or a perfumed product.

3. The method of claim 1, wherein the compound is methyl trans-2,6,6-trimethyl-3-cyclohexene-1-carboxylate or methyl (1R,2S)-2,6,6-trimethyl-3-cyclohexene-1-carboxylate.

4. The method of claim 1, wherein the perfuming composition or perfumed product is in the form of a perfume or a cologne, a perfumed soap, a shower or bath gel, a shampoo, a body deodorant or antiperspirant, an ambient air deodorant, a liquid or solid detergent for textile treatment, a detergent composition or a cleaning product for dishes or varied surfaces, a fabric softener or a cosmetic preparation.

5. The method of claim 3, wherein the perfuming composition or perfumed product is in the form of a perfume or a cologne, perfumed soap, a shower or bath gel, a shampoo, a body deodorant or antiperspirant, an ambient air deodorant, a liquid or solid detergent for textile treatment, a detergent composition or a cleaning product for dishes or varied surfaces, a fabric softener or a cosmetic preparation.

* * * * *